(12) United States Patent
Åhnblad et al.

(10) Patent No.: US 12,245,921 B2
(45) Date of Patent: Mar. 11, 2025

(54) NASAL PLUG

(71) Applicant: Hogne AB, Nacka (SE)

(72) Inventors: Susanne Åhnblad, Stockholm (SE); Peter Åhnblad, Muskö (SE)

(73) Assignee: HOGNE AB, Nacka (SE)

(*) Notice: Subject to any disclaimer, the term of this patent is extended or adjusted under 35 U.S.C. 154(b) by 970 days.

(21) Appl. No.: 17/062,589

(22) Filed: Oct. 4, 2020

(65) Prior Publication Data

US 2021/0015683 A1   Jan. 21, 2021

Related U.S. Application Data

(63) Continuation of application No. PCT/SE2020/050491, filed on May 13, 2020.

(30) Foreign Application Priority Data

May 13, 2019   (SE) .................................... 1950566-8

(51) Int. Cl.
    *A61F 13/20*   (2006.01)
(52) U.S. Cl.
    CPC ...... *A61F 13/2005* (2013.01); *A61F 13/2042* (2013.01)
(58) Field of Classification Search
    CPC ... A62B 23/06; A61F 13/2005; A61F 13/2042
    See application file for complete search history.

(56) References Cited

U.S. PATENT DOCUMENTS

| | | | |
|---|---|---|---|
| 4,052,983 A * | 10/1977 | Bovender | A62B 23/06 55/DIG. 35 |
| 6,768,040 B1 | 7/2004 | Sessions et al. | |
| 10,143,477 B2 | 12/2018 | Hsu | |
| 10,736,792 B1 * | 8/2020 | Fischell | A61F 13/55175 |
| 2003/0106555 A1 * | 6/2003 | Tovey | A61F 5/08 128/205.27 |
| 2004/0127843 A1 | 7/2004 | Tu | |
| 2005/0288620 A1 | 12/2005 | Shippert | |
| 2007/0277832 A1 * | 12/2007 | Doshi | A61M 16/06 128/207.18 |
| 2016/0256715 A1 * | 9/2016 | Chao | A62B 23/06 |
| 2018/0289383 A1 | 10/2018 | Fischell | |

(Continued)

FOREIGN PATENT DOCUMENTS

| | | |
|---|---|---|
| CN | 2203139 Y | 7/1995 |
| CN | 105 056 375 A | 11/2015 |
| DE | 102011110583 A1 | 2/2013 |

(Continued)

*Primary Examiner* — Rebecca E Eisenberg
*Assistant Examiner* — Rachel O'Connell
(74) *Attorney, Agent, or Firm* — Ballard Spahr LLP

(57) ABSTRACT

Nasal plug for treatment of nosebleed in a subject, comprising: a body adapted to fit into a nostril of the subject, the body comprising a first end arranged to face inward and a second end arranged to face outward during use; a hollow tubular member disposed inside the body and comprising a first opening facing inwardly and a second opening facing outwardly during use; wherein the tubular member further comprises a collar, adapted to prevent blood of a subject from escaping the body of the nasal plug, and wherein the collar is disposed completely inside the body.

10 Claims, 2 Drawing Sheets

(56) References Cited

U.S. PATENT DOCUMENTS

2020/0261752 A1\* 8/2020 Frank .................... A62B 23/06
2021/0008397 A1\* 1/2021 Strobl ................... A61M 11/02

FOREIGN PATENT DOCUMENTS

| FR | 3025713 A1 | 3/2016 |
| JP | 07308342 A | 11/1995 |
| RU | 2012367 C1 | 5/1994 |
| WO | 9911326 A1 | 3/1999 |
| WO | 0015165 A1 | 3/2000 |
| WO | 2010085196 A1 | 7/2010 |
| WO | 2018076118 A1 | 5/2018 |

\* cited by examiner

NASAL PLUG

This application is the continuation of international Application No. PCT/SE2020/050491, filed 13 May 2020, which claims the benefit of Swedish patent application SE 1950566-8, filed 13 May 2019, the entire contents of which are hereby incorporated by reference.

TECHNICAL FIELD

The present solution relates to a nasal plug for treatment of nosebleed.

BACKGROUND ART

Nosebleed, also known as epistaxis, is the common occurrence of bleeding from the nose. It is usually noticed when blood drains out through the nostrils. The vast majority of nosebleeds occur in the anterior (front) part of the nose from the nasal septum. This area, known as Kiesselbach's plexus, is richly endowed with blood vessels stemming from anastomosis of four arteries. Bleeding farther back in the nose is known as a posterior bleed and is usually due to bleeding from Woodruff s plexus, a venous plexus situated in the posterior part of inferior meatus. Posterior bleeds are often prolonged and difficult to control. They can be associated with bleeding from both nostrils and with a greater flow of blood into the mouth.

Nosebleeds can occur due to a variety of reasons. Some of the most common causes include trauma from nose picking, blunt trauma (such as a motor vehicle accident), or insertion of a foreign object (more likely in children). Relative humidity (including centrally heated buildings), respiratory tract infections, chronic sinusitis, rhinitis or environmental irritants can cause inflammation and thinning of the tissue in the nose, leading to a greater likelihood of bleeding from the nose. Most causes of nosebleed are self-limiting and do not require medical attention.

Most anterior nosebleeds can be stopped by applying direct pressure externally on the nose, which helps by promoting blood clots. In cases with prolonged nosebleed however, alternative treatments may be necessary, such as chemical cauterization of the blood vessels or nasal packing using gauze or foam polymer materials, often in the form of a plug, to increase the pressure on the vessels inside the nostril(s). Although effective in stopping nosebleed, nasal packing has the disadvantage of also blocking passage of air through the nostril(s), thus limiting the patient's ability to breathe through the nose. Nasal packing is therefore often associated with discomfort and not suitable for prolonged use. WO 2018/076118 discloses such a nose plug.

Another disadvantage associated with nasal packing is that after prolonged use, the packing material may become saturated and unable to soak up more blood. This could lead to undesirable dripping of excess blood from the nostril.

WO 2010/085196 discloses a nasal plug comprising a material that can be rolled, or compressed, and which may thereafter expand against a nasal passage thereby generating a pressure against it. The plug furthermore has a through-hole/tube for the passage of air, and a collar facilitating insertion and removal of the plug as well as preventing the plug from being sucked into the pharynx.

Thus, there is a need for an improved nasal plug which overcomes the disadvantages of the prior art.

SUMMARY OF INVENTION

It is an object of the solution to address at least some of the problems and issues outlined above. It is possible to achieve these objects and others by providing a nasal plug according to the present disclosure.

The above nasal plug may be configured and implemented according to different optional embodiments. Further possible features and benefits of this solution will become apparent from the detailed description below.

According to a first aspect, there is provided a nasal plug for the treatment of nosebleed in a subject. The nasal plug comprises a body adapted to fit into a nostril of the subject, the body comprising a first end arranged to face inward during use, and a second end arranged to face outward during use; a hollow tubular member disposed inside the body and comprising a first opening facing inwardly and a second opening facing outwardly during use; wherein the tubular member further comprises a collar, adapted to prevent blood of the subject from escaping the body of the nasal plug, and wherein the collar is disposed completely inside the body.

By providing a body with a hollow tubular member disposed therein, the present disclosure provides a dual solution of applying pressure to the blood vessels inside the nostril to stop the bleeding whilst maintaining an open passage for air to allow the subject to breathe without impediment. Furthermore, the collar on the tubular member forms a stop which effectively retains any excess blood emerging from the body of the nasal plug when saturated, thus preventing dripping. In this way, a compact nasal plug is achieved. Additionally, the stiffness of the collar stabilises the body of the nasal plug and also acts like an umbrella to push the body outwardly to stabilise and aid in applying outwardly directed pressure on the body which in turn increases the pressure applied on the site of the nosebleed in the nostril of the subject.

In a preferred embodiment, the body comprises a recess adapted to receive the tubular member and the collar. The recess may be substantially cylindrical to accommodate the tubular member in a snug fit.

In a preferred embodiment, the collar of the tubular member is cupped, with a concave side facing the first end of the body and a convex side facing the second end of the body. The cupped shape of the collar forms a bowl which retains the excess blood away from the edge of the collar to prevent it from escaping.

In a preferred embodiment, the tubular member protrudes from the second end of the body. The protruding second (proximal) end of the tubular member thus provides a grip allowing the subject to easily handle the nasal plug during insertion into and removal from the nostril.

In a preferred embodiment, a first end of the tubular member is disposed proximally of the first end of the body. In other words, the body extends further distally than the tubular member such that the first and distalmost end of the tubular member is substantially sunk into the body. By disposing the tubular member proximally of the first end of the body, the risk of injuring the nasal mucosa during insertion is reduced.

In a preferred embodiment, the body of the nasal plug is coated with a substance to be inhaled by the subject. The substance may comprise a pharmaceutical and/or an aroma compound, e.g. a haemostatic agent to promote haemostasis and/or menthol which has a cooling/soothing effect and may increase airflow through the nostril as well as acting as a local anaesthetic. When the subject inhales through the nasal plug, the air passes through the tubular member. As a result, near the first opening a local vacuum is formed which acts to draw the substance out from the body of the nasal plug such that it is mixed with the inhaled air.

An additional advantage with the collar is that it prevents the substance to be inhaled by the subject from exiting the nasal plug. When the subject exhales through the nasal plug, the air again passes through the first opening of the tubular member. Conversely to inhalation, the pressure in the nostril interior or proximal to the nasal plug increases. A small part of the exhaled air together with the substance will then enter the body of the nasal plug but the collar acts to retain the substance in the body.

In a preferred embodiment, the body is made from a resilient foam material. The resilient foam material absorbs the blood from the subject and regains its original shape after insertion in the nostril due to its excellent resilient properties, thereby ensuring that the nasal plug remains in close contact with the walls of the nostril during use.

In a preferred embodiment, the width of the collar in the widest transverse extension of the collar is substantially equal to or greater than the width of the body such that the collar when disposed in the body will stretch and push the body outwardly. Hence, the width of the collar will push the body outwardly along the transverse extension. Thus, the nasal plug braces against the lateral wall of the nostril and increases the pressure against the site of the nosebleed, e.g. Kiesselbach's plexus.

In a preferred embodiment, the tubular member is made from a flexible thermoplastic material. The thermoplastic material of the tubular member is preferably slightly stiffer than the material of the body, yet sufficiently flexible to avoid damage and discomfort during insertion and use. Preferably, the tubular member is resilient, striving to return to its original straight shape in order to provide a passage for the subject to breathe through.

In a preferred embodiment, a cross-section of the body and/or the collar has an oval shape. The oval shape is arranged to conform to the shape of the nostril to provide a snug, comfortable fit of the nasal plug during use.

In a preferred embodiment, the body is bell-shaped. The bell shape is arranged to conform to the shape of the nostril to provide a snug, comfortable fit of the nasal plug during use The aspects and embodiments described herein are freely combinable with each other.

BRIEF DESCRIPTION OF DRAWINGS

The solution will now be described, by way of example, with reference to the accompanying drawings, in which.

DESCRIPTION OF EMBODIMENTS

In the following, a detailed description of the different embodiments of the solution is disclosed with reference to the accompanying drawings. All examples herein should be seen as part of the general description and are therefore possible to combine in any way in general terms. Individual features of the various embodiments may be combined or exchanged unless such combination or exchange is clearly contradictory to the overall function of the implementation.

Briefly described, the present disclosure relates to a nasal plug 1 arranged to be inserted into the nostril 2 of a subject in order to stop a nosebleed. In the context of the present disclosure, the terms 'distal' and 'proximal' when referring to the nasal plug 1 and its components should be interpreted from the point of view of a person handling the nasal plug 1, regardless whether the subject suffering from nosebleed and the person handling the nasal plug 1 is the same or different persons.

Figure 1A:
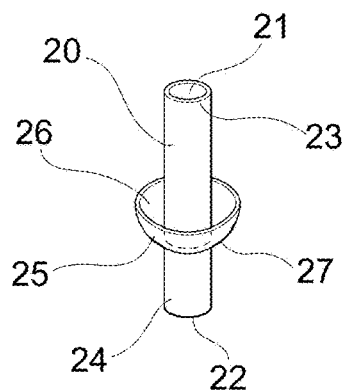
FIGS. 1A and 1B are perspective front and side views of a tubular member of a nasal plug according to one embodiment of the present disclosure.
Figure 1B:
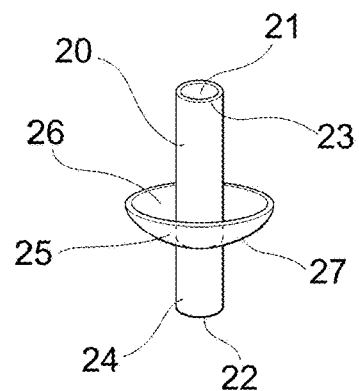

In FIGS. 1A and 1B, perspective views from the front and from the side are shown, respectively, of the tubular member 20 intended to be used in conjunction with the nasal plug 1 according to the present disclosure. The hollow tubular member 20 comprises a substantially cylindrical tube with a first opening 21 in a first end 23 and a second opening 22 in a second end 24 thereof. Additionally, the tubular member 20 comprises a collar 25 arranged on the external surface and extending outwardly. In one embodiment, the collar 25 is shaped like a cup, with a concave side 26 facing towards the first end 23 and a convex side 27 facing towards the second end 24. In one embodiment, the collar 25 is oval or elliptic, wherein the width when viewed from the front in FIG. 1A is given by the minor axis of the ellipse, and when viewed from the side in FIG. 1B is given by the major axis of the ellipse. I.e. the widest transverse extension of the collar 25 corresponds to the major axis of the ellipse. In one embodiment, the tubular member 20 comprises a flexible material, e.g. a thermoplastic material which is flexible yet provides a certain stiffness.

Figure 2A:
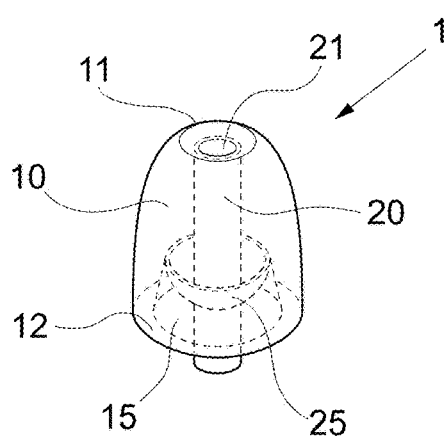
FIGS. 2A and 2B are sectional front and side views of a nasal plug with the tubular member according to one embodiment of the present disclosure.
Figure 2B:
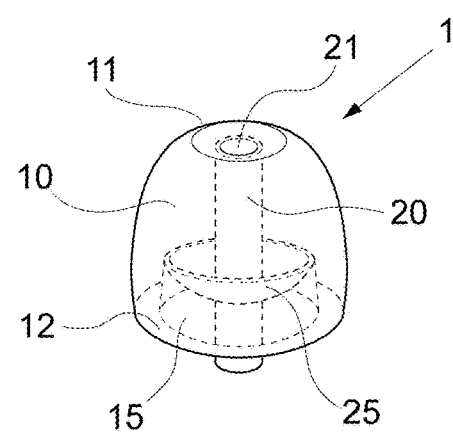

In FIGS. 2A and 2B, the nasal plug 1 according to the present disclosure is illustrated as viewed from the front and side, respectively. The nasal plug 1 comprises a body 10 and the hollow tubular member 20 disposed inside the body 10. The body 10 comprises a first end 11 and a second end 12 which substantially coincide or correspond with the first and second ends 21, 22, respectively, of the hollow tubular member 20 when inserted. The first end 11 of the body 10 is arranged to face inwardly when inserted into the nostril 2 of the subject during use. Conversely, the second end 12 is arranged to face outwardly during use. As such the first opening 21 of the tubular member 20 faces inwardly and the second opening 22 faces outwardly during use of the nasal plug 1.

As may be seen in FIGS. 2A and 2B as well as 3C, the collar 25 of the tubular member 20 fits into a recess 15 formed in the body 10 and facing towards the second end 12. The collar 25 forms a stop against the body 10 in the recess 15. The recess 15 may have a distal cylindrical portion which is narrow to fit snugly against the tubular member 20, and a wider proximal portion which is shaped to accommodate the collar 25.

In one embodiment, the body 10 comprises a resilient foam material adapted to absorb liquid, i.e. blood from the subject. Examples of suitable materials for the body 10 include polyurethane foam, polyether foam, (poly) ethylene-vinyl acetate (EVA/PEVA) foam, foam materials from forestry and agricultural by products based on organic cellulose or hemi-cellulose and special woven cotton, so called cotton-foam.

In one embodiment, the body 10 is coated with a haemostatic agent to promote blood clotting and stop bleeding.

Examples of suitable haemostatic agents include calcium alginate naturally present in e.g. brown algae (i.e. seaweed extracts), glycine, calcium, kaolin, zeolite, topical microfibrillar collagen and chitosan derived from shells of shrimp and other sea crustaceans.

In one embodiment, the body 10 is coated with an aroma compound to be inhaled by the subject. Examples of suitable aroma compounds include menthol, peppermint, lubricating oils such as sesame oil, Aloe vera or liquid paraffin which lubricate the mucosa in the nostril to prevent dehydration and formation of cracks or fissures and reduce the risk of rebleeding. When the subject inhales through the nasal plug 1, the air passes through the tubular member 20. As a result, near the first opening 21 a local vacuum is formed which acts to draw the substance out from the body 10 of the nasal plug 1 such that it is mixed with the inhaled air.

When the subject exhales through the nasal plug 1, the air again passes through the first opening of the tubular member 20. Conversely to inhalation, due to the reduced diameter of the tubular member 20 compared to the nostril, the pressure in the nostril proximal to the nasal plug 1 increases. A small part of the exhaled air together with the substance will enter the body 10 of the nasal plug 1 but the collar 25 acts to retain the substance in the body 10. Thus, the collar 25 prevents the substance to be inhaled by the subject from exiting the nasal plug 1, but instead retaining the substance in the body 10.

The nasal plug 1 and/or body 10 may in one embodiment have an oval-shaped cross-section as illustrated in FIGS. 2A and 2B, wherein the width of the nasal plug 1 is greater in the transverse extension corresponding to the major axis of the collar 25 as shown in FIG. 2B (side view). In one embodiment, the nasal plug 1 and/or body 10 is bell-shaped with a substantially cylindrical central portion, wherein the first end 11 is substantially hemispherical or dome-shaped and the second end 12 is flared outwardly. In one embodiment, the width of the collar 25 corresponding to the major axis of the oval shape is substantially equal to or greater than the width of the body 10. Thus, the collar 25 when inserted into the recess 15 will stretch and push the body 10 outwardly. Thus, the nasal plug 1 will brace against the lateral wall of the nostril to increase the pressure against the bleed site, e.g. Kiesselbach's plexus.

The tubular member 20 and the body 10 have substantially equal length, although in one embodiment the tubular member 20 is slightly offset from the body 10 such that the first end 23 of the tubular member 20 is arranged proximal to the first end 11 of the body 10, and the first opening 21 is sunk into the body 10. In this way, the second (distal) end 23 of the tubular member 20 is shielded inside the body 10 of the nasal plug 1 during insertion, to reduce the risk of damaging the nasal mucosa. In one embodiment, the tubular member 20 protrudes from the second end 12 of the body 10, i.e. the second (proximal) end 24 of the tubular member 20 extends further proximally than the body 10 to provide a grip when handling the nasal plug 1 during insertion into and removal from the nostril 2.

Figure 3A:
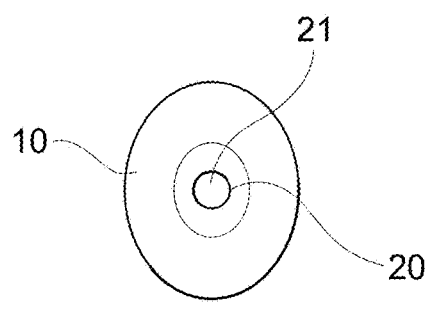
FIGS. 3A and 3B are top and bottom views of a nasal plug with the tubular member according to one embodiment of the present disclosure.
Figure 3B:
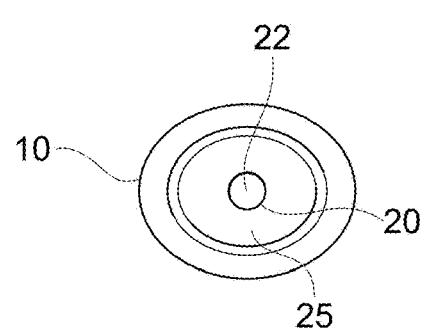
Figure 3C:
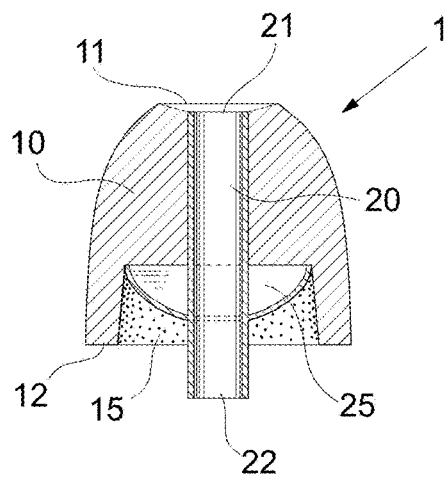
FIG. 3C is a cross-sectional view of a nasal plug with the tubular member according to one embodiment of the present disclosure.

FIGS. 3A and 3B show the nasal plug 1 as seen from above (FIG. 3A) and below (FIG. 3B). Note that the collar 25 is only visible from below. FIG. 3C shows the nasal plug 1 in cross-section.

Figure 4A:
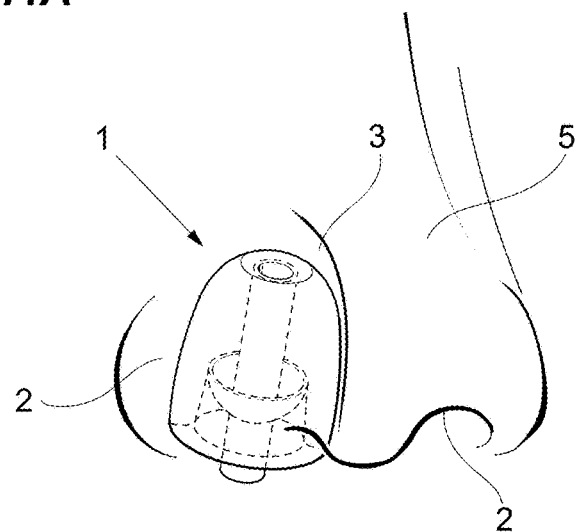
FIGS. 4A and 4B are front and side cutaway views of the nasal plug according to one embodiment of the present disclosure in use inserted in a nostril of a subject.
Figure 4B:
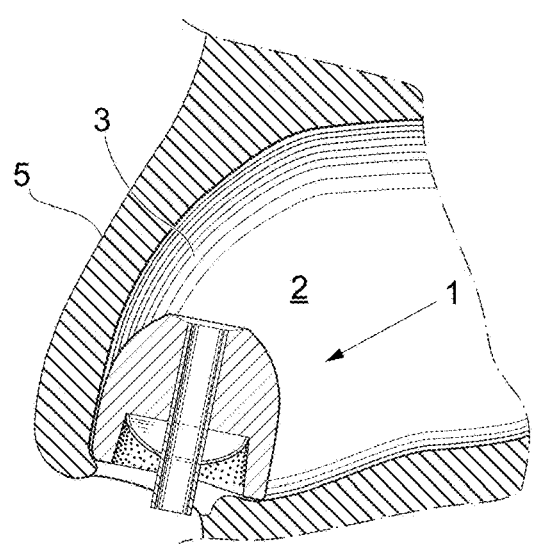

Turning now to FIGS. 4A and 4B, the nasal plug 1 according to the present disclosure is shown inserted into the nostril 2 of the nose 5 of a subject in a front and side view, respectively. Illustrated in FIG. 4A is the approximate site of Kiesselbach's plexus 3 in the nostril 2, located in the anteroinferior part of the nasal septum. As mentioned above, four arteries anastomose in this area forming a vascular plexus. About 80-90% of nosebleeds occur in Kiesselbach's plexus as it is exposed to the drying effect of inspiratory currents and to finger nail trauma.

The nasal plug 1 according to the present disclosure provides an effective treatment of nosebleed in that the absorbent body 10 applies direct pressure to the site of the nosebleed due to the resilient properties of the body 10 and absorbs the blood exiting the wound site. In cases of excessive and/or prolonged bleeding, the collar 25 forms a stop which effectively prevents blood from escaping the body 10 and thus avoids dripping from a saturated nasal plug 1. Additionally, the collar 25 acts like an umbrella to push the body 10 outwardly to stabilise and aid in applying pressure on the walls of the nostril 2.

At the same time, the tubular member 20 provides a fluid passage for air which enables the subject to continue breathing through the nose 5 even with the nasal plug 1 inserted in the nostril 2.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled in the art, and that the scope of the presently described concept is accordingly not to be limited. Reference to an element in the singular is not intended to mean "one and only one" unless explicitly so stated, but rather "one or more". Moreover, it is not necessary for an apparatus or method to address each and every problem sought to be solved by the presently described concept, for it to be encompassed hereby.

The invention claimed is:

1. Nasal plug for treatment of nosebleed in a subject, comprising:
   a body adapted to fit into a nostril of the subject, the body comprising a first end arranged to face inward and a second end arranged to face outward during use; and
   a hollow tubular member disposed inside the body of the nasal plug and comprising a tubular portion having a first opening facing inwardly and a second opening facing outwardly during use;
   wherein the hollow tubular member further comprises a collar extending radially outward from the tubular portion and adapted to prevent blood of a subject from escaping the body of the nasal plug,
   wherein the body of the nasal plug defines a recess adapted to receive the collar and at least a portion of the tubular portion, and
   wherein the collar is disposed inside the recess defined by the body of the nasal plug such that a rim of the collar defined by a radially outermost surface of the collar contacts an inner wall of the body defining the recess.

2. The nasal plug according to claim 1, wherein the collar of the hollow tubular member is cupped, with a concave side facing the first end of the body and a convex side facing the second end of the body.

3. The nasal plug according to claim 1, wherein the hollow tubular member protrudes from the second end of the body.

4. The nasal plug according to claim 1, wherein a first end of the hollow tubular member is disposed proximally of the first end of the body.

5. The nasal plug according to claim 1, wherein the body of the nasal plug is coated with a substance to be inhaled by the subject.

6. The nasal plug according to claim 1, wherein the body is made from a resilient foam material.

7. The nasal plug according to claim 6, wherein the width of the collar in the widest transverse extension of the collar is substantially equal to or greater than the width of the body such that the collar when disposed in the body will stretch and push the body outwardly.

8. The nasal plug according to claim 1, wherein the hollow tubular member is made from a flexible thermoplastic material.

9. The nasal plug according to claim 1, wherein a cross-section of the body and/or collar has an oval shape.

10. The nasal plug according to claim 1, wherein the body is bell-shaped.

* * * * *